(12) United States Patent
Schaffran et al.

(10) Patent No.: US 7,806,692 B2
(45) Date of Patent: Oct. 5, 2010

(54) IMPLANT ABUTMENT CLIPS

(75) Inventors: Allan Schaffran, Toronto (CA); Andy Doug-Lun Wong, Toronto (CA); Robert G. Dickie, King City (CA)

(73) Assignee: Implant Ingenuity Inc., King City, Ontario (CA)

( * ) Notice: Subject to any disclaimer, the term of this patent is extended or adjusted under 35 U.S.C. 154(b) by 124 days.

(21) Appl. No.: 11/644,719

(22) Filed: Dec. 22, 2006

(65) Prior Publication Data

US 2008/0153059 A1 Jun. 26, 2008

(51) Int. Cl.
*A61C 8/00* (2006.01)
(52) U.S. Cl. ...................................... 433/173
(58) Field of Classification Search ............. 433/141, 433/173, 72, 75, 162–163, 172–176, 218–223, 433/153–154
See application file for complete search history.

(56) References Cited

U.S. PATENT DOCUMENTS

| | | | |
|---|---|---|---|
| 1,127,236 A | 2/1915 | Harbridge | |
| 1,712,196 A | 5/1929 | Burger et al. | |
| 3,604,488 A | 9/1971 | Wishart et al. | |
| 4,704,929 A | 11/1987 | Osada | |
| 4,744,273 A | 5/1988 | Bartok, Jr. | |
| 5,158,458 A | 10/1992 | Perry | |
| 5,423,860 A | 6/1995 | Lizardi et al. | |
| 5,462,436 A | 10/1995 | Beaty | |
| 5,692,904 A | 12/1997 | Beaty et al. | |
| 5,927,979 A | 7/1999 | Misch et al. | |
| 6,116,125 A | 9/2000 | McLeod | |
| 6,227,856 B1 * | 5/2001 | Beaty et al. | ........... 433/172 |
| 6,244,141 B1 | 6/2001 | Han | |
| 6,280,192 B1 | 8/2001 | Groll et al. | |
| 6,328,746 B1 | 12/2001 | Gambale | |

(Continued)

FOREIGN PATENT DOCUMENTS

WO     WO 97/06930     2/1997

(Continued)

OTHER PUBLICATIONS

Mark Hafwell D.D.S. M.S.C., Dental Implants: A Different Perspective (Part 2), Implant Practice, US Edition, May 2009, vol. 2, No. 2, pp. 34-41.

*Primary Examiner*—Cris L Rodriguez
*Assistant Examiner*—Matthew M Nelson
(74) *Attorney, Agent, or Firm*—Sand & Sebolt

(57) ABSTRACT

An abutment clip for use in a dental implant system for orienting an abutment relative to features on a patient's teeth and jawbone so that a prosthesis, which is attachable to the abutment, will be correctly oriented. The abutment clip comprises a housing that includes a chamber sized to receive the abutment therein. The housing has at least one position indicator provided at one end thereof. The dentist engages the abutment clip over the abutment when it is still attached to a manufacturer's plaster model. He notes the position of the indicator on the housing in reference to features on the model and then detaches the abutment clip, abutment and abutment screw as a unit from the model. The combined abutment clip, abutment and screw are then positioned on an implant post in the patient's jaw bone and the position indicator is used to verify the orientation of the abutment before it is secured to the implant post.

31 Claims, 13 Drawing Sheets

U.S. PATENT DOCUMENTS

| | | | |
|---|---|---|---|
| 6,701,812 B1 * | 3/2004 | Sawamura | 81/453 |
| 6,824,386 B2 * | 11/2004 | Halldin et al. | 433/173 |
| 6,854,972 B1 * | 2/2005 | Elian | 433/173 |
| 6,997,086 B1 | 2/2006 | Graham | |
| 7,100,476 B1 | 9/2006 | Feit | |
| 2002/0106610 A1 * | 8/2002 | Hurson | 433/173 |
| 2005/0266379 A1 | 12/2005 | Kumar et al. | |
| 2006/0075856 A1 | 4/2006 | Tilton | |
| 2006/0278050 A1 | 12/2006 | Hsiao | |
| 2007/0295173 A1 | 12/2007 | Swartz | |

FOREIGN PATENT DOCUMENTS

| | | |
|---|---|---|
| WO | WO 97/24996 | 7/1997 |
| WO | WO 00/28914 | 5/2000 |
| WO | WO 03/037207 | 5/2003 |
| WO | WO 03/101332 | 12/2003 |

* cited by examiner

IMPLANT ABUTMENT CLIPS

BACKGROUND OF THE INVENTION

1. Technical Field

This invention generally relates to dentistry. More particularly, the invention relates to dental implants. Specifically, the invention relates to an abutment clip that is detachably engageable over an abutment and includes at least one position indicator thereon that aids the dental surgeon in correctly orienting an abutment on an implant post.

2. Background Information

Over the last few decades dental technology has made great strides in providing improved ways to give people more natural-appearing and better secured artificial teeth or bridgework. (For the sake of clarity, both single artificial teeth and bridgework will be referred to hereinafter as "a prosthesis"). One of those improved technologies utilizes dental implants. A dental implant is a small titanium screw or bolt that is secured into the jaw bone to act as an anchor for a prosthesis. The implants are installed by drilling a small hole in the patient's jaw bone and then screwing an implant post into the bone surrounding the hole. The implant post is then covered with a flap of skin and the patient is sent away for a number of months to allow time for osseointegration to occur, i.e., for the living bone of the jaw to fuse to the implant post. The patient then returns to the dental surgeon who attaches an abutment to the implant post. The abutment is essentially a support that is secured to the implant post and extends upwardly and outwardly away from the jawbone. The prosthesis is then slipped over the abutment and is secured thereover by an adhesive cement.

A number of dental implant systems have been developed by different manufacturers, but most systems provide an implant post that has a specifically shaped post head and an internally threaded bore. The abutment is designed to interlock with the implant post and therefore includes a lower recess that receives the head of the implant post therein. A small screw is then inserted through the abutment and into the bore of the implant post. The screws used in these procedures are very small and are usually only about ¼ inch long. They are therefore extremely difficult to handle as the dental surgeon has to place the screw into a hole on the abutment and then hold both the screw and abutment on the implant post with one finger while trying to line up and begin to engage the threads on the screw with the other hand. Once the thread is started and there is no danger of dropping the screw and abutment, the dental surgeon will use a speed wrench to tighten the screw. When the abutment is secured in place, the prosthesis is attached to the abutment by way of an adhesive cement.

One of the key problems with the above procedure is the extremely limited access in various areas of the mouth, such as the region around the rear molars. The difficulty of this process is further compounded if the position for the implant is in the upper rear part of the mouth between two teeth. This position is more difficult because the dental surgeon faces the effects of gravity and, because the position of installation is toward the back of the mouth, there is the further complication of limited vision and access. If the prosthesis is to be installed between two teeth, the dental surgeon also only has access to the abutment from two sides because of the adjacent teeth. It is easier to position an implant to replace the rearmost molar in the mouth as this location permits the dental surgeon to have access to the abutment from three different sides. The dental surgeon is always concerned that the screw and abutment will fall out of the jawbone before the threads are engaged and that the patient might then accidentally swallow or inhale them. It is therefore commonplace for dental surgeons to position a cloth or other obstruction toward the back of the mouth to catch and retrieve any fallen components. It has been noted by the present inventors that a screw or other small component falls out during the initial thread capture as much as 20% of the time.

A second problem experienced by dental surgeons when doing this procedure is the problem of correctly orienting the abutment during installation so as to ensure that the prosthesis will end up in the correct orientation relative to the surrounding teeth. When either a single artificial tooth or bridgework is to be manufactured, an impression is made of the patient's jawbone after the implant posts have been installed. The impression is used to help the laboratory to produce a model. The model is used to produce a prosthesis that is correctly shaped, positioned and oriented relative to the teeth that are permanently seated in the jawbone. Dental implant systems are made so that the connection between the abutment and the implant post will reduce or prevent any rotation of the prosthesis in the mouth. In order to achieve this, some implant posts are manufactured with hexagonally shaped post heads, some have square post heads and others are triangular. However, this also means that the abutment can be engaged on the post head in more than one orientation. For example, if the abutment/implant connection is triangular in shape, then there are three possible orientations that the abutment may assume on the implant post. If the abutment/implant connection is square in shape, there are four possible positions that the abutment may assume on the implant post head. If the abutment/implant connection is hexagonal, then there are six possible orientations. What is subtle but very important to understand is that the abutment shape is rarely axially aligned with the implant post that is installed in the bone. This is because the implant post will be installed at whatever angle the surgeon feels is the best placement for that bolt in the jawbone. The dental lab must figure out the correct shape and angle that the abutment should be at so as to cause the prosthesis to be correctly aligned in the jawbone with any adjacent teeth. Furthermore, the angle of the abutment also needs to provide the dental surgeon with the necessary clearance to lower and glue the prosthesis into place, while still allowing for sufficient clearance from the adjacent teeth. So the abutment is custom made and carefully oriented on a plaster model.

Once the prosthesis is manufactured, it is returned to the dental surgeon attached to the actual plaster model that was made from the impression. The prosthesis is attached to the plaster model using the custom-made abutment. The dental surgeon has to remove the prosthesis, take special note the rotational position of the abutment on the model, detach the abutment from the model and then secure the abutment to the implant post in exactly the same rotational position in the patient's jaw. So, if the connection between the abutment and the implant post is a square connection, there will be four different possible positions for the abutment and the dental surgeon has to select the correct one of those four possible positions. This does not sound too difficult, but the abutment is so small and the shape and angle so subtle that it is difficult to get the abutment correctly oriented in the mouth. To make matters worse, the dental surgeon must also control and turn the tiny screw that it inserted through the abutment to set the abutment firmly on the implant post.

There is therefore a need in the art for an improved device for helping to correctly orient and install dental abutments on implant posts.

SUMMARY OF THE INVENTION

The device of the present invention comprises an abutment clip for use in a dental implant system. The abutment clip is used to orient an abutment relative to features on a patient's teeth and jawbone so that a prosthesis, which is attachable to the abutment, will be correctly oriented. The abutment clip comprises a housing that includes a chamber sized to receive the abutment therein. The housing has at least one position indicator that is provided at one end thereof. The dentist engages the abutment clip over the abutment when it is still attached to a manufacturer's plaster model. He notes the position of the indicator on the housing in reference to features on the model and then detaches the abutment clip, abutment and abutment screw as a unit from the model. The combined abutment clip, abutment and screw are then positioned on an implant post in the patient's jaw bone and the position indicator is used to verify the orientation of the abutment before it is secured to the implant post.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Figure 1:
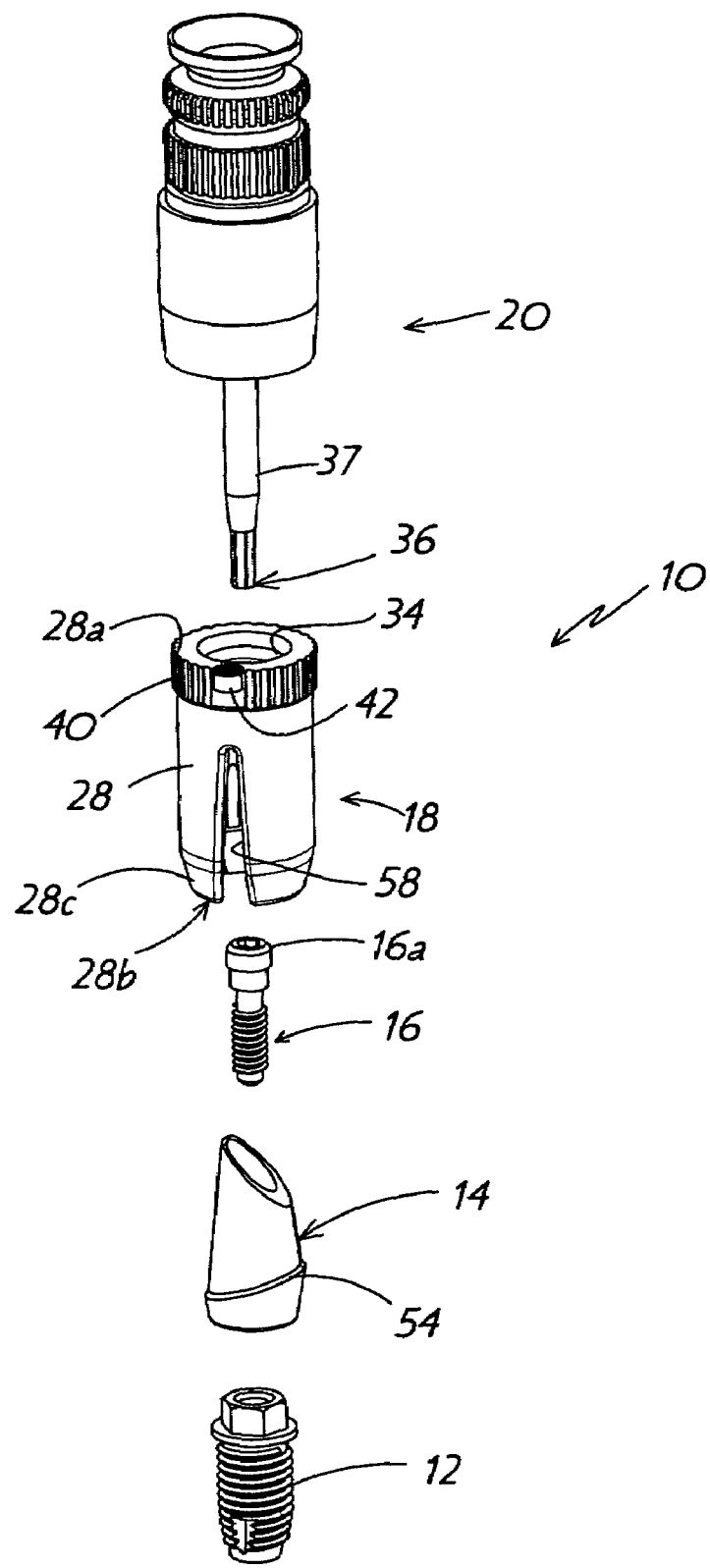
FIG. 1 is an exploded partial perspective view of the dental screwdriver, the abutment clip of the present invention, the screw and abutment into which it is being installed.

Referring to FIGS. 1-14, there is shown a dental implant system 10 comprising an implant post 12, an abutment 14, an abutment screw 16, an abutment clip 18 in accordance with the present invention, and a screwdriver 20 for securing the various components together. System 10 is used to install a prosthesis, such as artificial tooth 22 (FIG. 5) into the jaw of a patient. In the attached figures, the jaw illustrated may represent a model 24a (FIG. 2) of a patient's jaw that is used for transporting a manufactured abutment 14 and prosthesis 22 from a laboratory to a dental surgeon, or it may be the actual jaw 24b (FIG. 5) into which the implant and abutment are secured.

Figure 2:
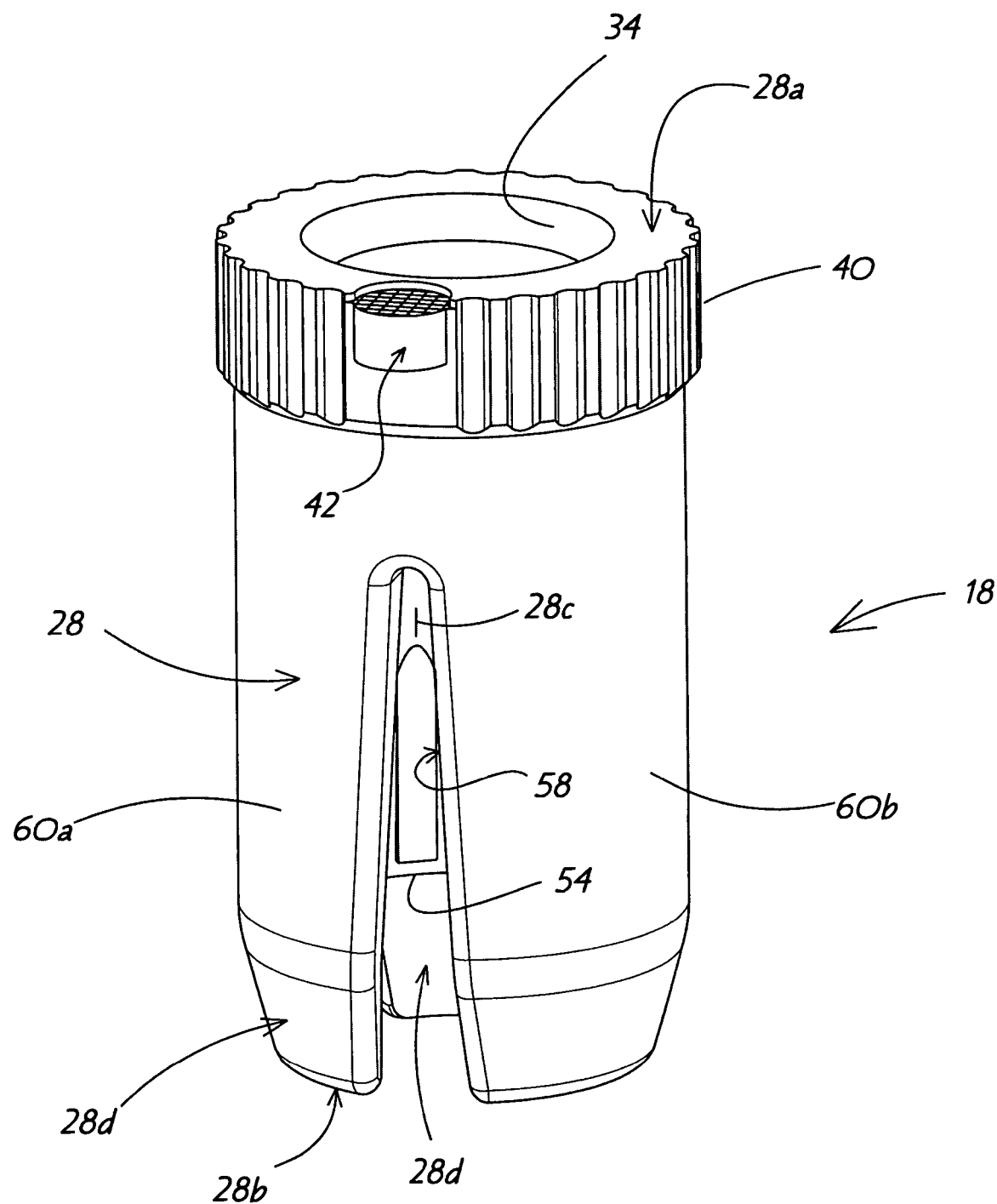
FIG. 2 is a partial perspective view of the abutment clip in accordance with the present invention.
Figure 3:
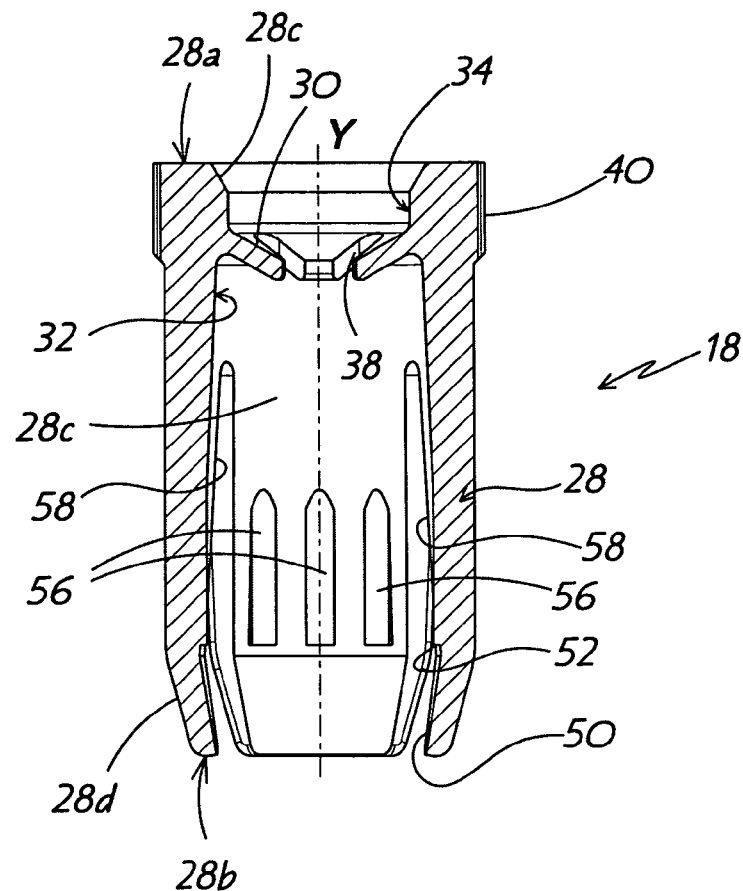
FIG. 3 is a cross-sectional front view of the abutment clip of FIG. 2.
Figure 4:
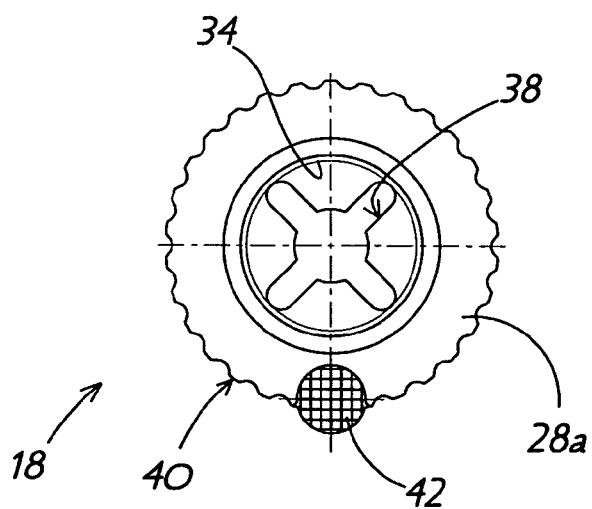
FIG. 4 is a top view of the abutment clip of FIG. 2.

As shown in FIGS. 2-4, and in accordance with a specific feature of the present invention, an abutment clip 18 is provided to enable a dental surgeon to more accurately identify the orientation that abutment 14 has in jaw 24a and to replicate that orientation when the abutment 14 and prosthesis 22 and positioned in the jaw 24b of the patient.

Still referring to FIGS. 2-4, abutment clip 18 comprises a housing having a generally cylindrical peripheral wall 28, an end wall 30 and longitudinal axis "Y". Peripheral wall 28 has a first and a second end 28a, 28b and end wall 30 is positioned intermediate first and second ends 28a, 28b. End wall 30 is however closer to first end 28a than to second end 28b. End wall 30 and peripheral wall 28 surround and define a chamber 32 that is sized to receive abutment 14 therein. End and peripheral walls 30, 28 further define a recess 34 that is sized and shaped so as to direct a tip 36 of screwdriver 20 downwardly and inwardly toward an aperture 38 in end wall 30. Thus, the inner surface 28c of peripheral wall 28 proximate first end 28a includes at least two annular stepped-regions of a progressively narrower diameter. Aperture 38 is configured to receive at least a portion of tip 36 therethrough. In the preferred embodiment of the invention, aperture 38 is shaped to receive the tip of a Phillips screwdriver therein, but it will be understood that aperture 38 could be of any other shape that would specifically engage a differently shaped screwdriver tip such as slotted, hex, Robertson, Pozidriv (® of Phillips Screw Company of Wakefield, Mass.); and Torx (® of Textron Industries, Inc. of Rockford Ill.). First end 28a of peripheral wall 28 also includes a grasping area that enables the dental surgeon to more easily hold the clip 18 against rotation. Grasping area preferably comprises a knurled surface 40 that is provided on the exterior surface of peripheral wall 28 proximate first end 28a. The knurled surface 40 may be an integral part of peripheral wall 28 or may be a separate textured region that is applied over the exterior surface of peripheral wall 28, as shown in FIG. 3.

In accordance with another specific feature of the present invention, first end 28a of abutment clip 18 is provided with one or more position indicators 42 thereon. Indicators 42 preferably are positioned at least partially on both the upper surface and side surface of first end 28a of clip 18 so that the dental surgeon can more easily see the same. Indicators 42 may be any suitable type of marking device such as a shaped detent, a slot, a colored region or a combination of the same. Furthermore, more than one indicator 42 can be provided around the circumference of first end 28a so that the dental surgeon has more than one reference point by which to orient the abutment 14 relative to the jaw 24 or to other teeth 44, 46, 48 that are adjacent the position in jaw 24 where abutment 14 is to be installed.

Still referring to FIGS. 2-4, in accordance with yet another feature of the present invention, clip 18 is provided with an abutment engaging area proximate second end 28b thereof.

Abutment engaging area includes an annular region 28d of peripheral wall 28 that tapers inwardly proximate second end 28b. Thus, the diameter of the opening 50 to chamber 32 is narrowed making it more difficult for abutment 14 to slide out of chamber 32. Furthermore, peripheral wall 28 of clip 18 is provided with one or more axial slots 58 that extend from second end 28b inwardly toward end wall 30 thereof. Preferably, more than one slot 58 is provided in peripheral wall 28 so that wall 28 is divided into opposing jaws, such as jaws 60a, 60b shown in FIG. 2. Jaws 60a, 60b are designed to act like pincers that open slightly to engage abutment 14 and then close again to grasp abutment 14 between them. If two slots 58 are provided in peripheral wall 28, then those slots 58 are disposed opposite each other. If three slots 58 are provided in peripheral wall 28 (such as in the version of abutment clip 18 shown in the drawings), then those slots 58 are positioned at equal distances around the circumference of peripheral wall 28.

An annular shoulder 52 is formed in the inner surface 28c of peripheral wall 28 proximate an inner end of tapered region 28d. Annular shoulder 52 is provided to interlock with a shoulder 54 on abutment 14. Inner surface 28c is also provided with a plurality of spaced-apart axial ribs 56. Ribs 56 preferably are formed inwardly of shoulder 52 but do not extend the entire length of chamber 32 up to end wall 30. Ribs 56 are provided to aid in gripping abutment 14 and to retard any rotational motion of abutment 14 within chamber 32.

Figure 5:
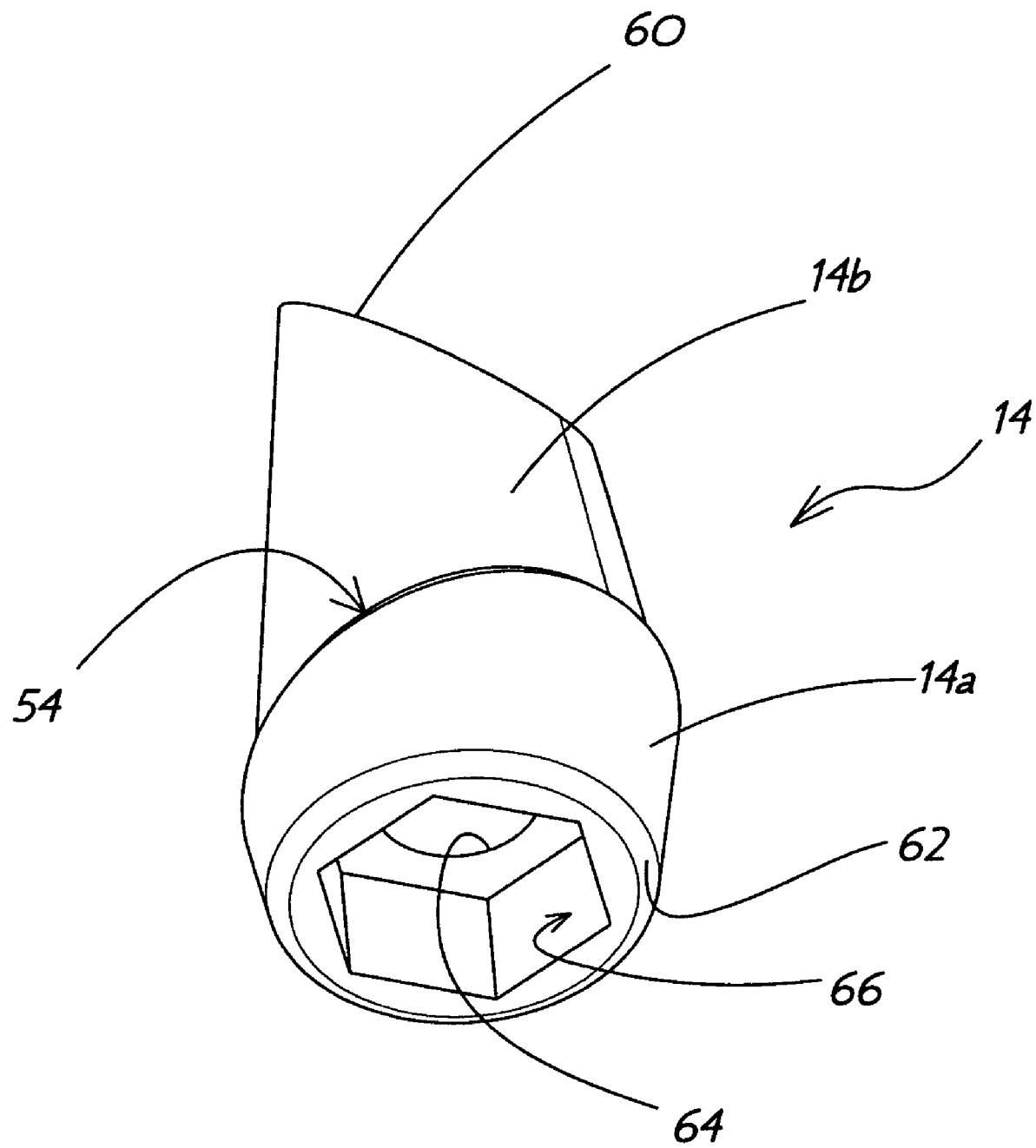
FIG. 5 is a bottom perspective view of an abutment showing a hex-shaped recess for engagement with the implant post.
Figure 6:
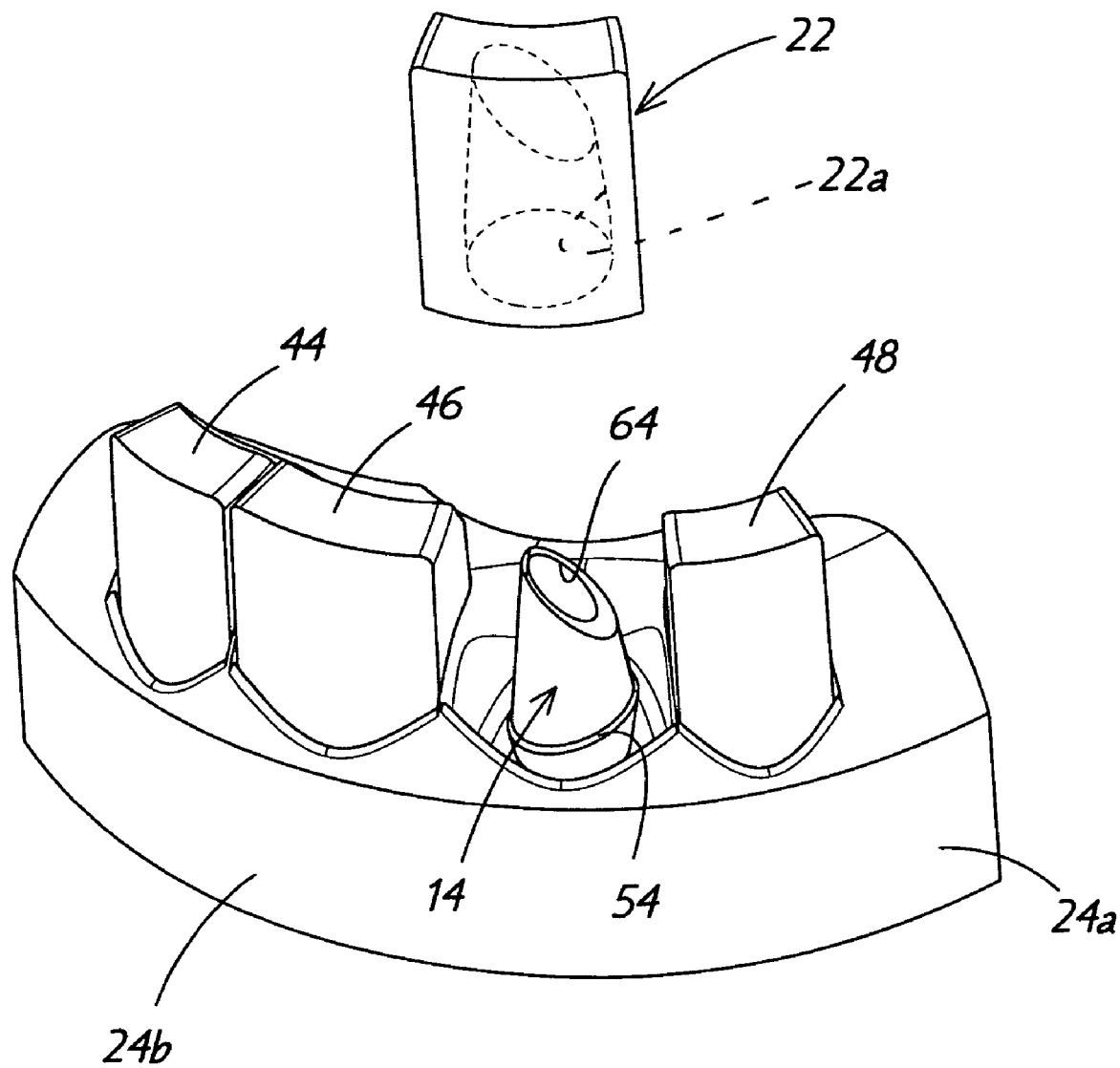
FIG. 6 is a perspective view of a plaster model or the patient's jaw with the abutment secured thereto and the prosthesis removed therefrom.
Figure 7:
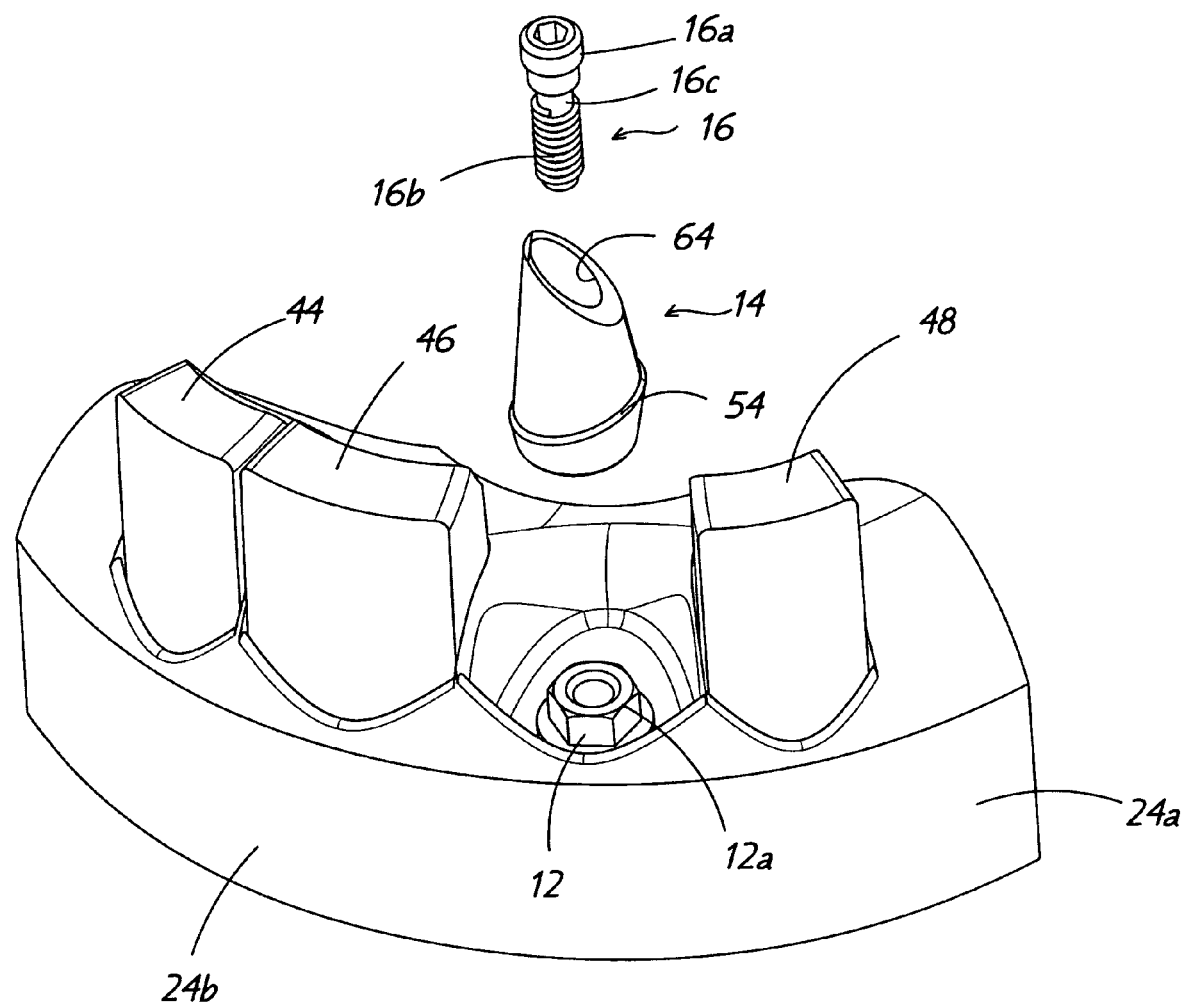
FIG. 7 is a partially exploded perspective view of the plaster model or the patient's jaw showing the abutment, the screw and an implant post.

The abutment clip 18 of the present invention is used to engage and retain the abutment 14. It will be understood that abutment 14, shown in greater detail in FIG. 5, is merely illustrative of any shaped and configured abutment that are engageable by abutment clip 18. Thus, abutment 14 has an upper end 60 and a lower end 62 with a bore 64 extending from the upper to the lower ends 60, 62. Bore 64 is sized to receive screw 16 therethrough. As mentioned previously, abutment 14 also includes a shoulder 54 formed on an annular lower region 14a that is of a greater diameter than the upper region 14b. Lower end 62 is also provided with a shaped recess 66 to receive and engage the head 68 of implant post 12 therein. FIG. 5 illustrates recess 66 as hexagonally shaped so that it may engage with a hexagonally shaped head of implant post 12. It will be understood that recess 66 may be of a different configuration so as to engage differently shaped implant post heads. So, for example, some dental implant systems have square implant post heads and in that instance, the abutment to be used therewith will have a square recess in its lower end. The overall shape and size of abutment 14 are designed and custom built by the denture manufacturer to correctly orient and support the prosthesis 22 that is to be installed thereover. Consequently, abutment clip 18 will engage a variety of differently shaped abutments 14 and retain the same within chamber 32. However, because the size of the abutment 14 may vary, with the diameters of upper and lower regions 14b, 14a thereof being larger or smaller as necessary, the dental surgeon will have a range of different sized abutment clips 18 to engage differently sized abutments 14, and will select the appropriate clip for the job.

Figure 8:
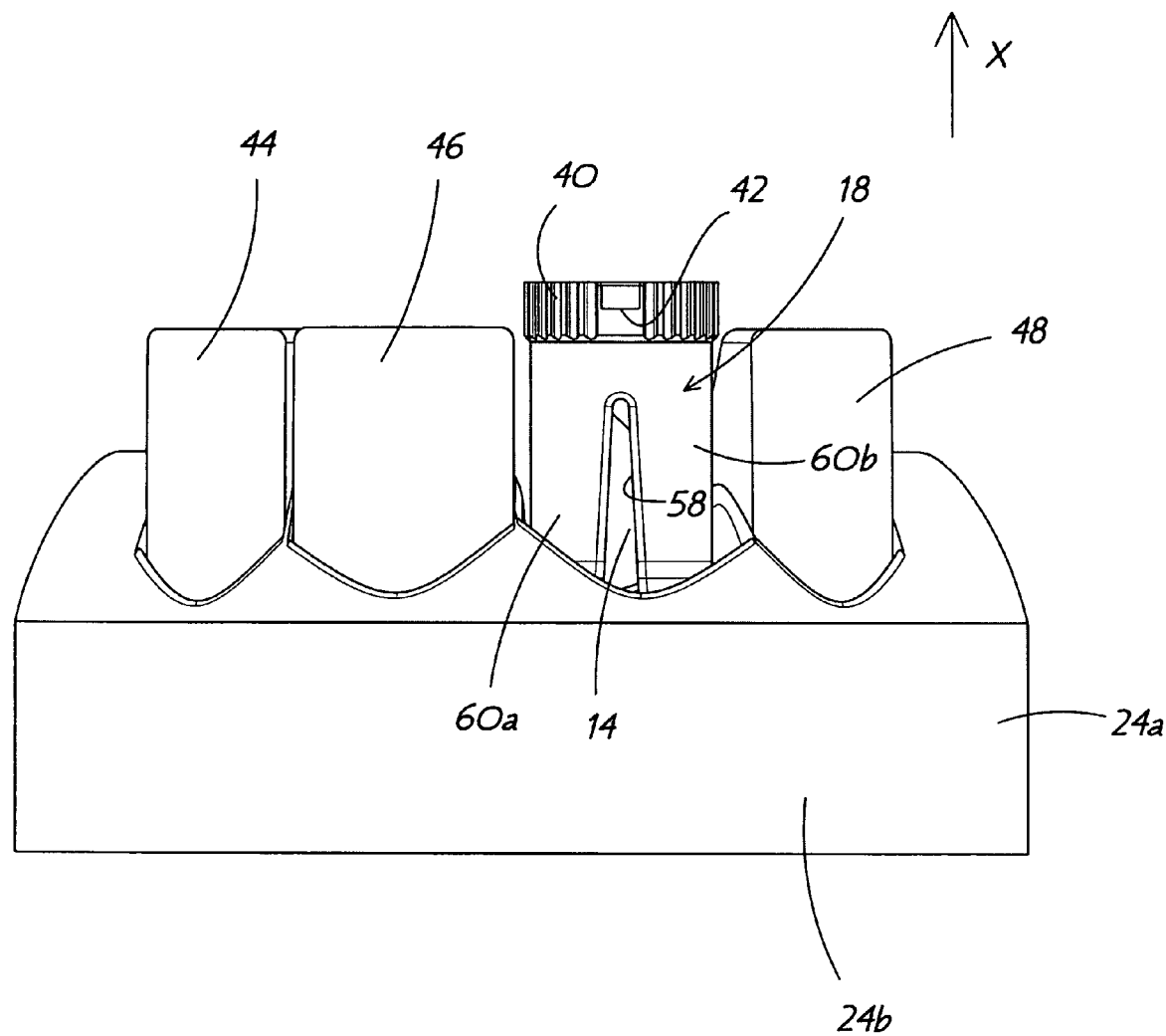
FIG. 8 is a front view of the plaster model or the patient's jaw with the abutment clip in engagement with the abutment.
Figure 9:
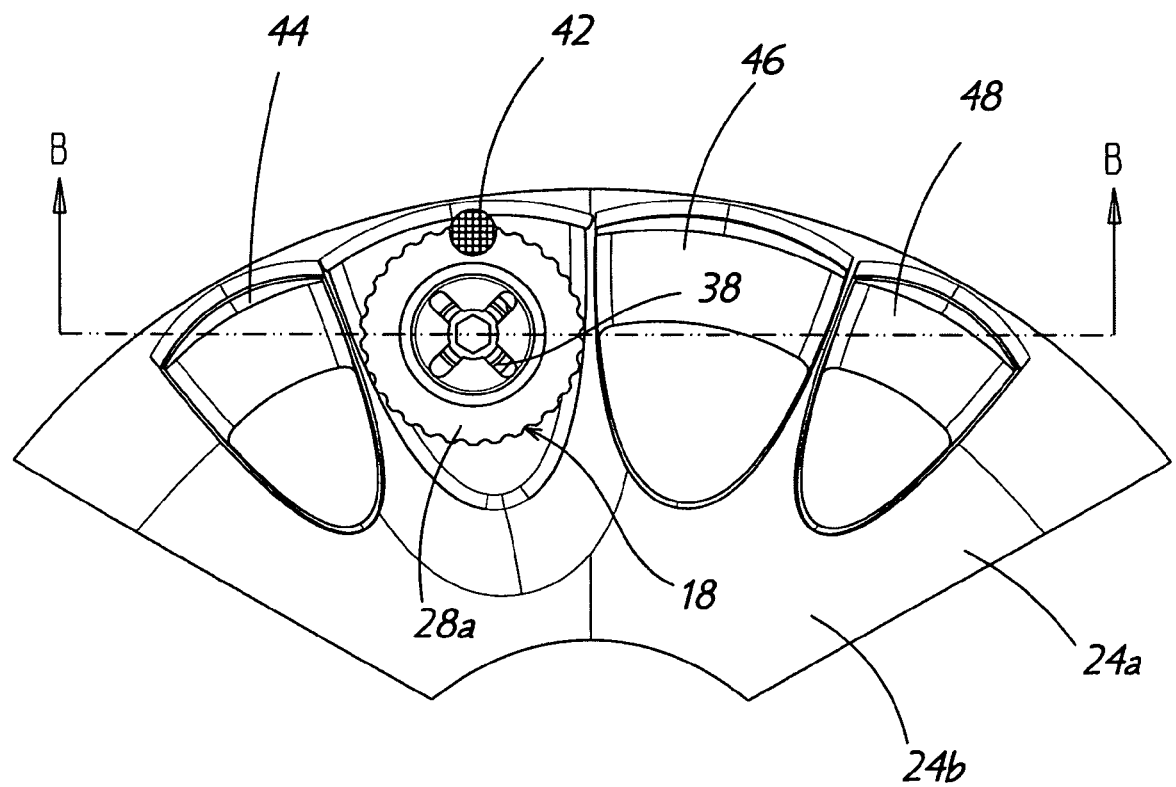
FIG. 9 is a top view of the plaster model or the patient jaw with the abutment clip in engagement with the abutment.
Figure 10:
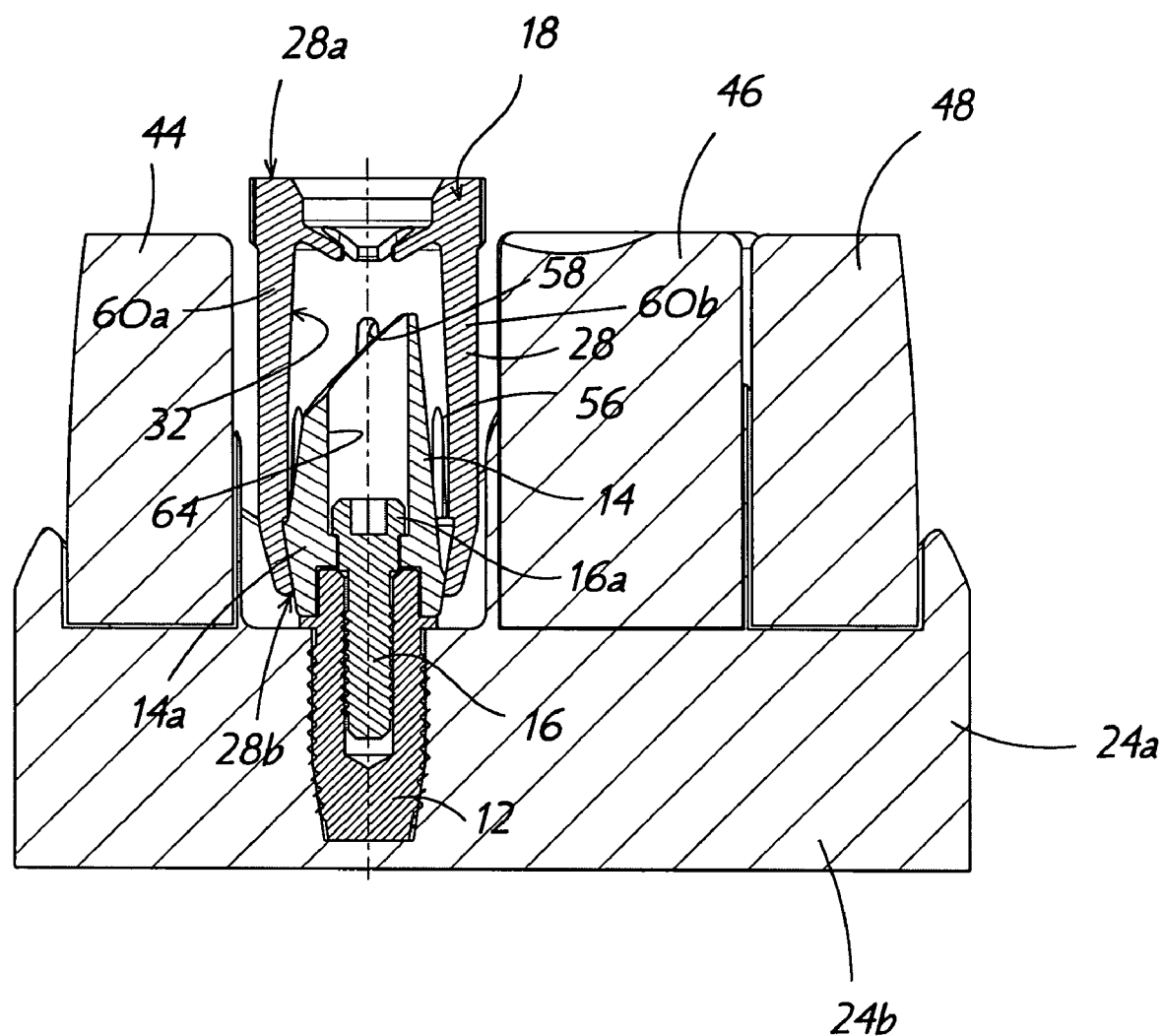
FIG. 10 is a cross-sectional view of the plaster model or the patient jaw through line B-B of FIG. 9.
Figure 11:
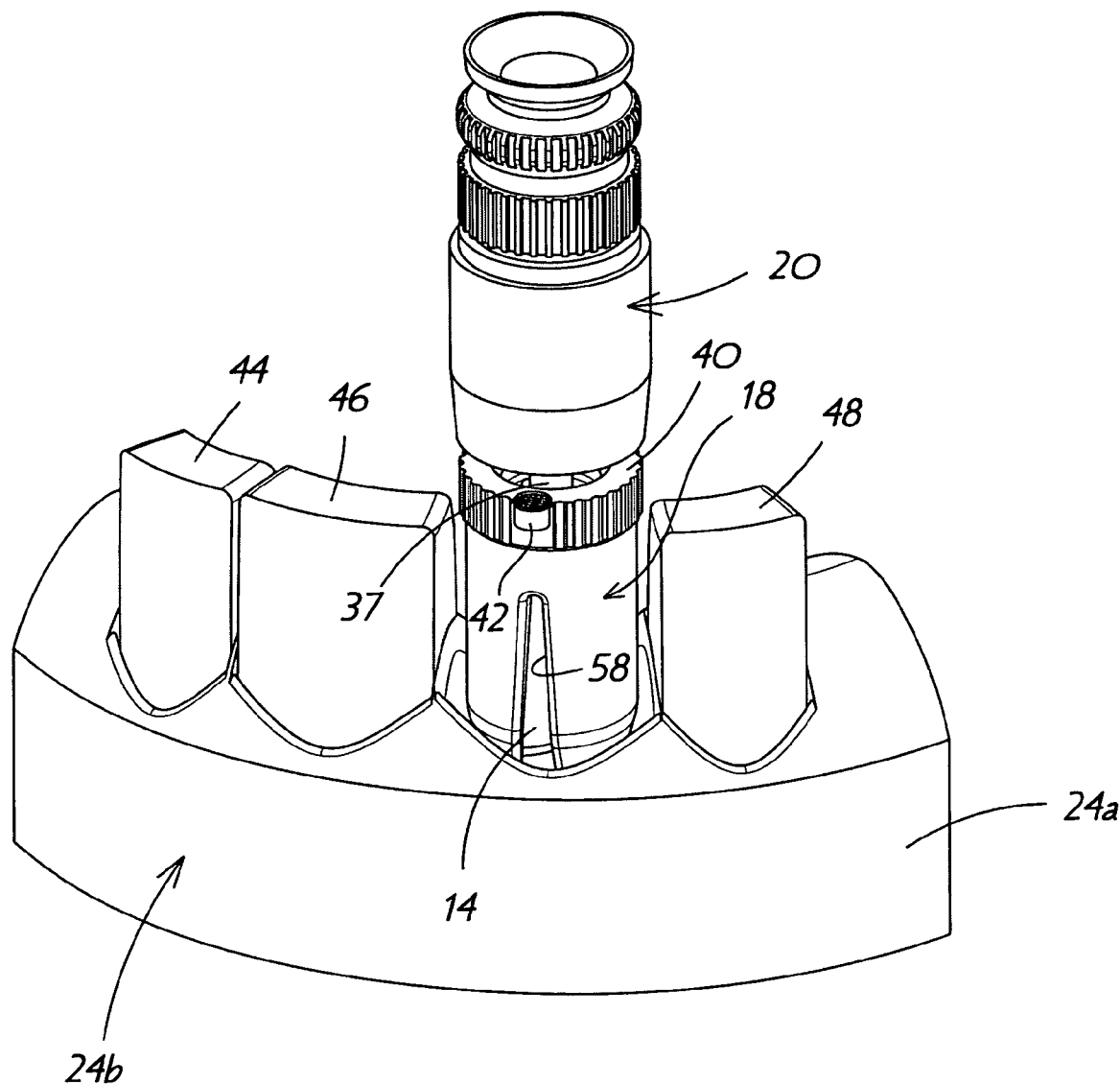
FIG. 11 is a perspective view of the plaster model or the patient jaw showing the screwdriver engaging the abutment and abutment clip.
Figure 12:
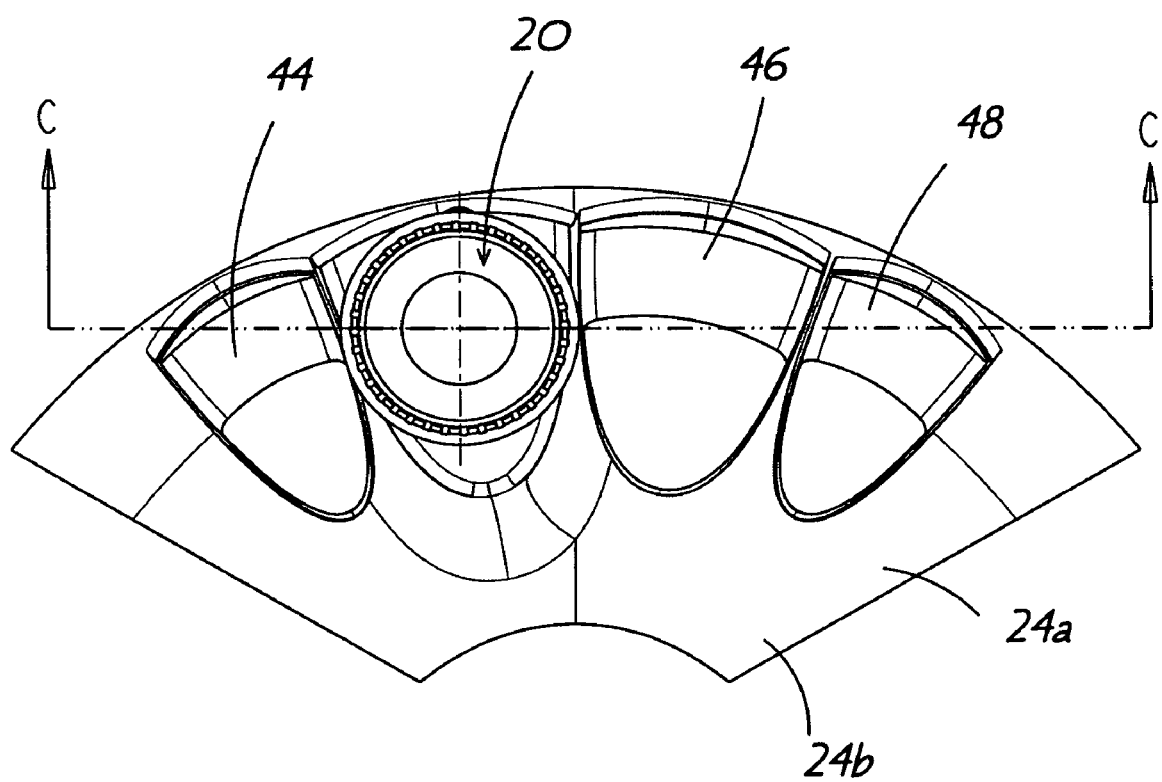
FIG. 12 is a top view of the plaster model or the patient jaw shown in FIG. 11.
Figure 13:
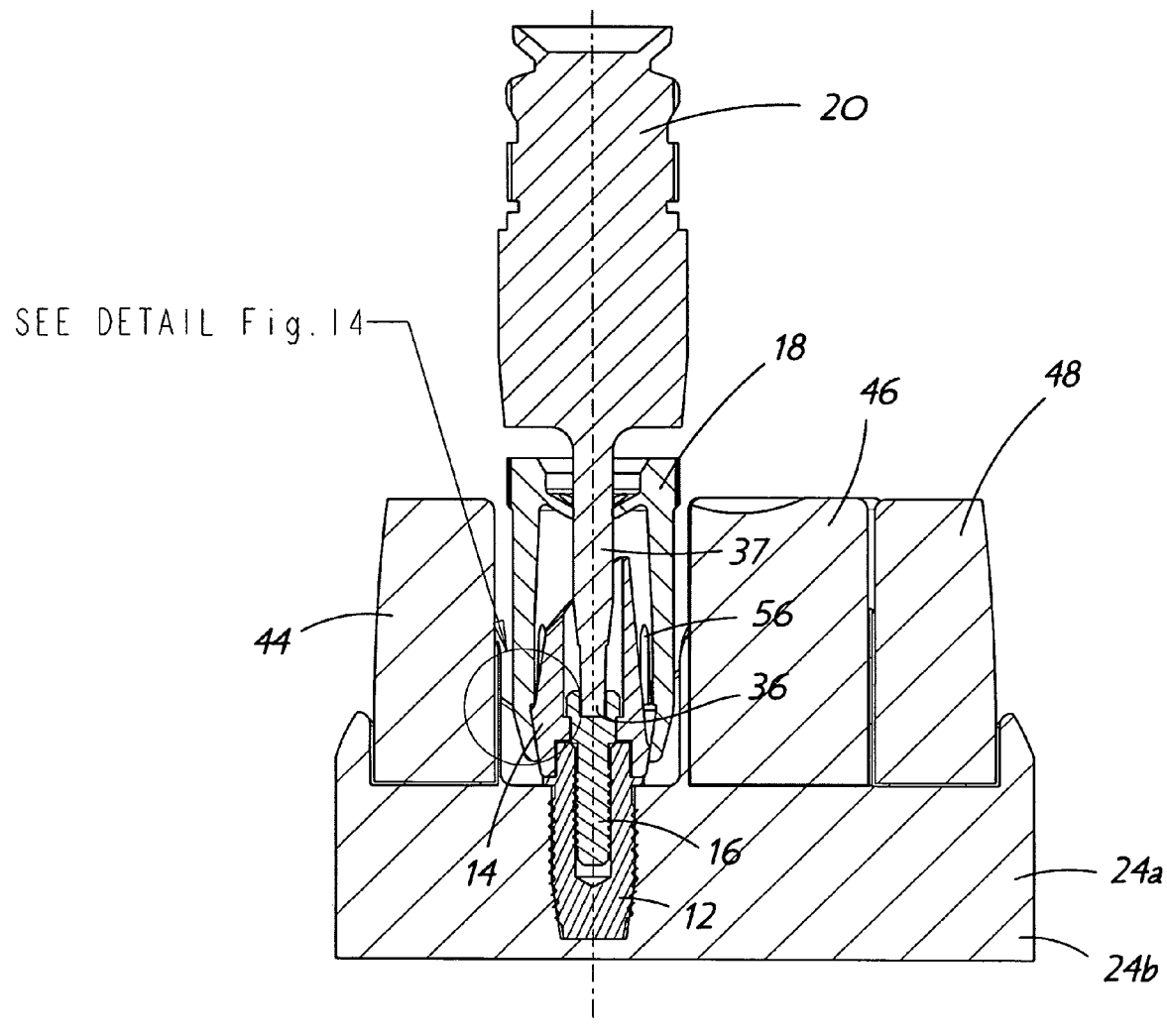
FIG. 13 is a cross-sectional view of the plaster model or the patient jaw through line C-C of FIG. 12.
Figure 14:
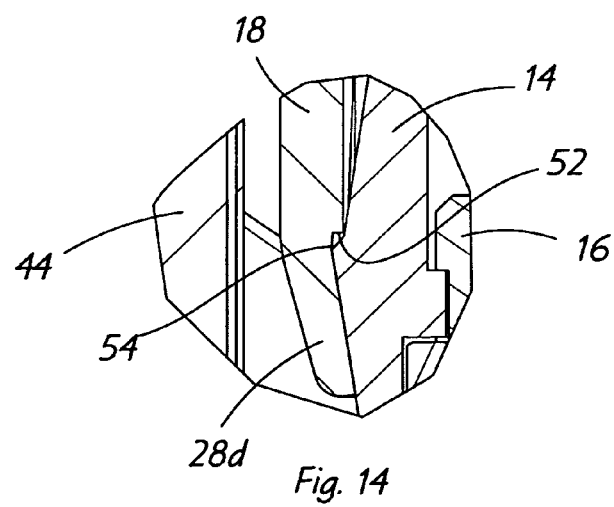
FIG. 14 is an enlarged cross-sectional view of the highlighted region of FIG. 13.
Figure 15:
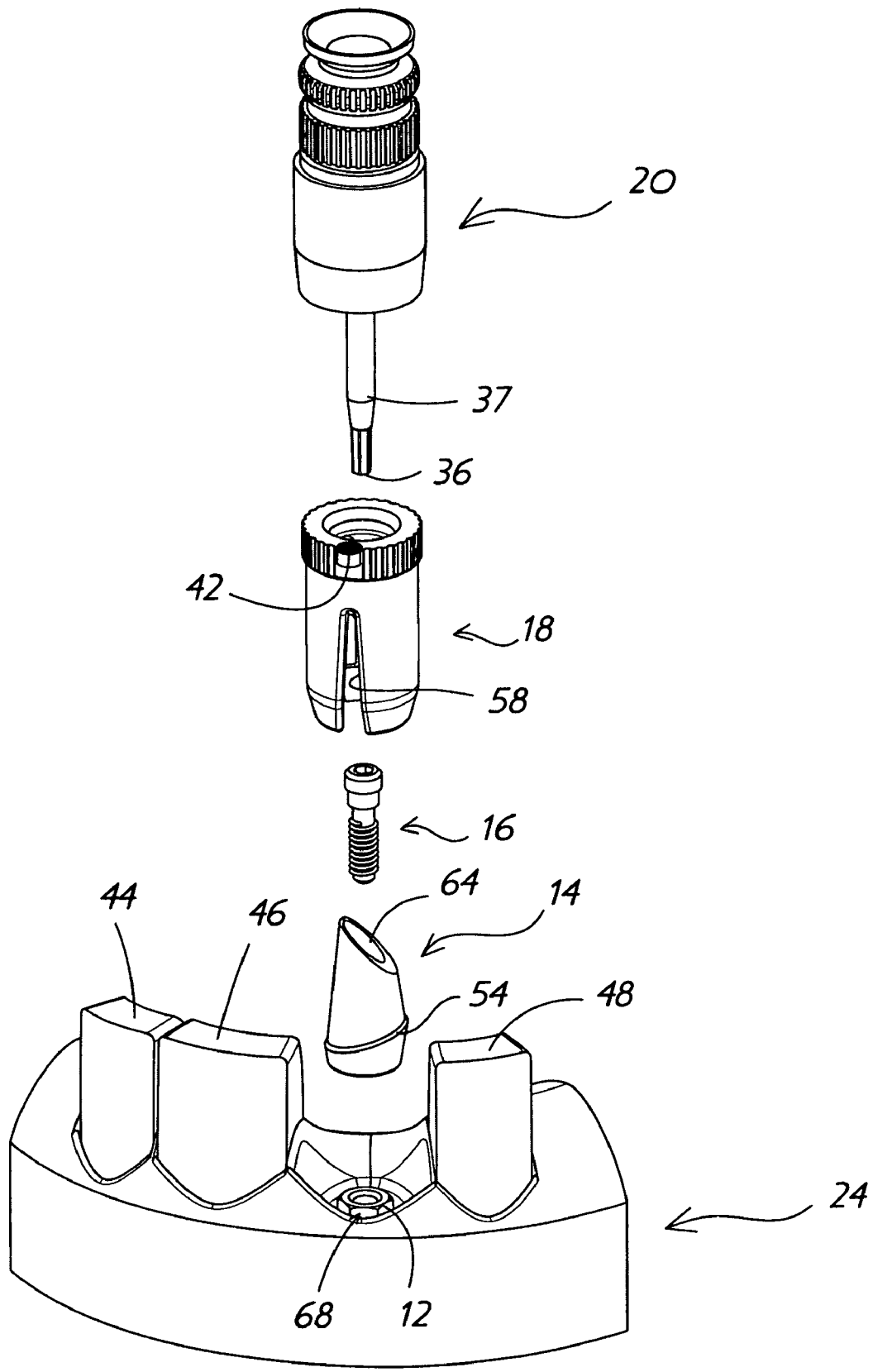
FIG. 15 is an exploded perspective view of the plaster model or the patient jaw showing the implant post, the abutment, the screw, the abutment clip and the screwdriver.

The abutment clip 18 of the present invention is used in the following manner. When the dental surgeon is sent the plaster model of the patient's jaw, the model (shown in FIGS. 6 & 7) has abutment 14 secured to jaw 24a via a screw 16 and an implant post 12a. Implant post 12a is substantially identical to the bolt 12 that has been previously implanted in the patient's jaw 24. The prosthesis 22 will typically be positioned over abutment 14, but is not physically secured thereto. The dental surgeon will remove prosthesis 22, take the appropriately sized abutment clip 18 and slide the same downwardly over abutment 14 (FIGS. 8-10). At this point, the surgeon will manipulate abutment clip 18 until indicator 42 is in a position that he can use to serve as a reference point for later installation of the abutment in the patient's mouth. That position will be noted by the surgeon in any manner appropriate to himself. At this stage, abutment clip 18 is engaged with abutment 14 in such a manner that shoulder 52 on clip 18 is interlocked with shoulder 54 on abutment 14. Furthermore, the jaws 60a, 60b are firmly in engagement with the lower portion 14a of abutment 14. Ribs 56 abut lower portion 14a and abutment 14 is tightly retained within abutment clip 18. At this point, abutment clip 18, screw 16 and abutment 14 form an abutment assembly that may be selectively engaged with implant post 12 or disengaged therefrom. The recess 66 on abutment 14 is presented at the second end 286 of abutment clip 18 for such engagement with implant post 12.

The dental surgeon grasps knurled portion 40 of abutment clip 18 and using a screwdriver 20, inserts the tip 36 and a portion of the shaft 37 thereof through aperture 38 in end wall 30, through bore 64 of abutment 14 and into engagement with head 16a of screw 16. It will be understood that while a dental screwdriver 20 is illustrated herein, any other suitable screwdriver, such as a jeweler's screwdriver can be used. The surgeon holds the knurled portion 40 of clip 18 to ensure that clip 18 and abutment 14 do not rotate when screw 16 is rotated as the position of abutment 14 in clip 18 needs to be maintained. Once screw 16 is loosened, the combined abutment 14, screw 16 and abutment clip 18 is removed from the jaw 24a of the plastic model.

The dental surgeon then positions the combined abutment 14, screw 16 and clip 18 in place in the patient's jaw 24b. In order to do this, he lowers clip 18 onto implant post 12 (FIG. 7) so that the head of said bolt 12 is received into recess 66 of abutment 14. Indicator 42 is used to orient abutment clip 18 in exactly the same position relative to teeth 44, 46, 48 that was noted on the plaster model. If the surgeon does not think the position is correct, the combined clip 18, abutment 14 and screw 16 is lifted off implant post 12 and is rotated slightly and re-engaged with bolt 12. Once the position of abutment clip 18 is correct, the screwdriver tip 36 is engaged with screw 16. The surgeon grips knurled portion 20 of clip 18 to ensure there is no rotation of the same when screwdriver 20 is activated. Screw 16 is rotated by screwdriver 20 so that the threads 16b on the shaft 16c thereof threadably engage the internal threads of implant post 12. Once abutment 14 is secured, screwdriver 20 is disengaged and an X-ray is taken of the patient's mouth to ensure that abutment 14 is in exactly the correct position and that it is fully seated on implant post 12. If this is found to be true, then screw 16 is torqued to the manufacturer's specifications in the known manner. The surgeon then removes abutment clip 18 by grasping knurled portion 40 and pulling clip 18 off of abutment 14 in the direction of arrow "X".

The dentist will then take the prosthesis 22 and apply a small amount of cement to the abutment 14 and/or interior of a hole 22a in prosthesis 22. The prosthesis 22 is then slidingly engaged over abutment 14 so that abutment 14 is received within hole 22a.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. An abutment clip for use in a dental implant system that includes an abutment for securing a prosthesis to an implant post; wherein said abutment clip comprises:
   a housing having a first end and a second end and a peripheral wall extending therebetween;
   a single position indicator provided on the peripheral wall proximate the first end of the housing; and wherein the housing is free of any other indicators;
   a chamber defined by the first end, the second end and the peripheral wall;
   a first opening into the chamber defined in the first end;
   a second opening into the chamber defined in the second end; and said second opening is adapted to receive the abutment therethrough;
   an abutment engagement area provided in the peripheral wall a spaced distance inwardly from the second end of the housing;
   a region of the peripheral wall extending between the abutment engagement area and the second end; and wherein said chamber is substantially of a first internal diameter from proximate the first end up to the abutment engagement area, and is of a second internal diameter at the abutment engagement area; said second diameter being greater than the first diameter; and wherein said chamber tapers in internal diameter along the region of the peripheral wall and proximate the second end said chamber is of an internal diameter that is substantially equal to the first internal diameter.

2. The abutment clip as defined in claim 1, wherein the position indicator originates in the first end of the housing and extends longitudinally for a distance along said peripheral wall, said position indicator being provided to permit a dental surgeon to orient the clip on the abutment and in the patient's jawbone.

3. The abutment clip as defined in claim 2, wherein the position indicator is selected from a group consisting of one or more of a detent, a recess, a line, a colored marker and a slot.

4. The abutment clip as defined in claim 1, wherein the housing is manufactured from a transparent plastic material, whereby an abutment retained therein is visible.

5. The abutment clip as defined in claim 1, wherein the peripheral wall has an interior surface and an exterior surface and the interior surface thereof includes an annular shoulder formed at an innermost end of the abutment engagement area where the internal diameter of the chamber changes from the first internal diameter to the second internal diameter and said annular shoulder is adapted to engage a shoulder on the abutment.

6. The abutment clip as defined in claim 1, wherein said housing includes an end wall proximate the first end thereof and the peripheral wall extends outwardly away from the end wall and terminates at the second end thereof; and the peripheral wall has an interior surface that surrounds the abutment-receiving chamber; and wherein the peripheral wall further includes a plurality of spaced apart longitudinally oriented ribs on the interior surface thereof that are adapted to contact an exterior surface of the abutment when it is received within the chamber.

7. The abutment clip as defined in claim 6, wherein the ribs are positioned between the abutment engagement area and the first end of the housing.

8. The abutment clip as defined in claim 1, wherein the region of the peripheral wall between the abutment engagement area and the second end has a length; and wherein the abutment engagement area is adapted to receive a shoulder of the abutment therein; and the region of the peripheral wall is adapted to extend for a distance beyond the shoulder and toward a distal end of the abutment; and wherein the length of the region of the peripheral wall is sufficient to enable the clip to retain the abutment therein during withdrawal and installation of the abutment in a jawbone.

9. The abutment clip as defined in claim 1, wherein the peripheral wall is of a first external diameter from adjacent the first end of the housing up to the abutment engagement area; and the housing is of a second external diameter at the second end, said second external diameter being smaller than the first external diameter; and wherein the region of the peripheral wall between the abutment engagement area and the second end tapers in external diameter.

10. The abutment clip as defined in claim 1, wherein the position indicator is disposed on the first end of the housing; and the first end of the housing includes a knurled surface and the position indicator comprises a slot that extends through at least a portion of the knurled surface.

11. The abutment clip as defined in claim 10, wherein the position indicator further includes a marking on an end wall at the first end of the housing adjacent the slot.

12. The abutment clip as defined in claim 1, wherein the position indicator comprises a detent that projects laterally outwardly away from the peripheral wall for a distance.

13. An abutment clip, for use in a dental implant system that includes an abutment for securing a prosthesis to an implant post; wherein said abutment clip comprises:
   a housing having a first end and a second end and a peripheral wall extending therebetween; wherein said housing includes a longitudinal axis extending between the first and second ends; and wherein said peripheral wall further includes at least one longitudinally aligned slot that extends from the second end of the housing inwardly toward the first end thereof;
   a single position indicator provided on the peripheral wall proximate the first end of the housing;
   a chamber defined by the first end, the second end and the peripheral wall;
   a first opening into the chamber defined in the first end;
   a second opening into the chamber defined in the second end; and said second opening is adapted to receive the abutment therethrough
   an abutment engagement area provided in the peripheral wall a spaced distance inwardly from the second end of the housing;
   a region of the peripheral wall extending between the abutment engagement area and the second end; and wherein said chamber is substantially of a first internal diameter from proximate the first end up to the abutment engagement area, and is of a second internal diameter at the abutment engagement area; said second diameter being greater than the first diameter; and wherein said chamber tapers in internal diameter along the region of the peripheral wall and proximate the second end said chamber is of an internal diameter that is substantially equal to the first internal diameter.

14. The abutment clip as defined in claim 13, wherein the peripheral wall includes at least two longitudinally aligned slots, each slot extending from the second end of the housing inwardly toward the end wall; whereby said peripheral wall comprises at least two jaws that are adapted to engage and retain the abutment therebetween.

15. An abutment clip for use in a dental implant system that includes an abutment for securing a prosthesis to an implant post; wherein said abutment clip comprises:

a housing having a first end and a second end and a peripheral wall extending therebetween; wherein said housing includes an end wall proximate the first end thereof and the peripheral wall extends outwardly away from the end wall and terminates at the second end thereof;

a single position indicator provided on the peripheral wall proximate the first end of the housing;

a chamber defined by the first end, the second end and the peripheral wall;

a first opening into the chamber defined in the first end, and wherein the first opening comprises an aperture in the end wall that is adapted to receive a portion of a shaft and tip of a screwdriver therethrough so as to engage a screw for securing the abutment to the implant post, and said first opening includes a substantially circular central region and a plurality of slots radiating radially outwardly away therefrom;

a second opening into the chamber defined in the second end; and said second opening is adapted to receive the abutment therethrouqh an abutment engagement area provided in the peripheral wall a spaced distance inwardly from the second end of the housing;

a region of the peripheral wall extending between the abutment engagement area and the second end; and wherein said chamber is substantially of a first internal diameter from proximate the first end up to the abutment engagement area, and is of a second internal diameter at the abutment engagement area; said second diameter being greater than the first diameter; and wherein said chamber tapers in internal diameter along the region of the peripheral wall and proximate the second end said chamber is of an internal diameter that is substantially equal to the first internal diameter.

16. An abutment clip abutment clip for use in a dental implant system that includes an abutment for securing a prosthesis to an implant post; wherein said abutment clip comprises:

a housing having a first end and a second end and a peripheral wall extending therebetween;

a single position indicator provided on the peripheral wall proximate the first end of the housing; wherein the position indicator comprises a detent that projects laterally outwardly away from the peripheral wall for a distance; wherein the position indicator originates in the first end of the housing and extends longitudinally for a distance along the peripheral wall; and the peripheral wall further includes an annular knurled surface that extends for substantially the same distance along the peripheral wall as the position indicator and the position indicator interrupts the knurled surface;

a chamber defined by the first end, the second end and the peripheral Wall;

a first opening into the chamber defined in the first end;

a second opening into the chamber defined in the second end; and said second opening is adapted to receive the abutment therethrough an abutment engagement area provided in the peripheral wall a spaced distance inwardly from the second end of the housing;

a region of the peripheral wall extending between the abutment engagement area and the second end; and wherein said chamber is substantially of a first internal diameter from proximate the first end up to the abutment engagement area, and is of a second internal diameter at the abutment engagement area; said second diameter being greater than the first diameter; and wherein said chamber tapers in internal diameter along the region of the peripheral wall and proximate the second end said chamber is of an internal diameter that is substantially equal to the first internal diameter.

17. The abutment clip as defined in claim 16, wherein the position indicator is free of knurling.

18. The abutment clip as defined in claim 16, wherein a portion of the position indicator is visible in the first end of the housing, and said visible portion is visually distinct from the rest of the first end of the housing.

19. An abutment transfer clip for use in a dental implant system that includes an abutment for securing a prosthesis to an implant post; wherein said abutment transfer clip comprising:

a housing having an upper end, a lower end and a longitudinal axis extending therebetween:

an upper wall at the upper end;

a peripheral wall extending downwardly from the upper wall and terminating at the lower end;

a single position indicator projecting laterally outwardly away from an exterior surface of the peripheral wall, and wherein the housing is free of any other indicators, a longitudinally aligned chamber defined by an interior surface of each of said peripheral and upper walls;

an aperture defined in said upper wall and providing access into said chamber; and an opening defined in the lower end of the housing and providing access into said chamber.

20. The abutment transfer clip as defined in claim 19, wherein the position indicator is provided on a portion of the peripheral wall proximate the upper end of the housing.

21. The abutment transfer clip as defined in claim 19, wherein the aperture in the upper wall includes a substantially circular central region with a plurality of slots that extend radially outwardly from the central region.

22. The abutment transfer clip as defined in claim 21, wherein an area of the upper wall disposed intermediate each pair of adjacent slots slopes downwardly and inwardly from the upper end of the housing toward the circular central region of the aperture.

23. The abutment transfer clip as defined in claim 22, wherein the aperture has four arms that extend equidistantly radially outwardly away from said circular central region.

24. The abutment transfer clip as defined in claim 19, further comprising at least one slot defined in the peripheral wall and extending from the lower end of the housing upwardly toward the upper end thereof, said slot being substantially parallel to the longitudinal axis of the housing.

25. The abutment transfer clip as defined in claim 19, wherein an annular region of the peripheral wall proximate the lower end tapers inwardly.

26. The abutment transfer clip as defined in claim 19, wherein the peripheral wall has an interior surface that surrounds and defines the interior chamber and the interior surface is provided with a plurality of ribs that are substantially parallel to the longitudinal axis of the housing and are spaced at intervals from each other.

27. The abutment transfer clip as defined in claim 26, wherein an annular region of the peripheral wall proximate the lower end tapers inwardly and the ribs originate above said annular region and terminate approximately midway between the upper and lower ends of the housing.

28. An abutment transfer clip for use in a dental implant system that includes an abutment for securing a prosthesis to an implant post; wherein said abutment transfer clip comprises:

a housing having an upper end, a lower end and a longitudinal axis extending therebetween:
- an upper wall at the upper end;
- a peripheral wall extending downwardly from the upper wall and terminating at the lower end;
- a single position indicator projecting laterally outwardly away from an exterior surface of the peripheral wall, wherein the position indicator is provided on a portion of the peripheral wall proximate the upper end of the housing; and wherein the portion of the peripheral wall is provided with knurling and said position indicator extends outwardly beyond said knurling
- a longitudinally aligned chamber defined by an interior surface of each of said peripheral and upper walls;
- an aperture defined in said upper wall and providing access into said chamber; and
- an opening defined in the lower end of the housing and providing access into said chamber.

29. The abutment transfer clip as defined in claim 28, wherein the position indicator is free of knurling.

30. The abutment transfer clip as defined in claim 29, wherein the position indicator originates in the upper wall of the housing and is disposed at an outer perimeter thereof.

31. The abutment transfer clip as defined in claim 30, wherein a region of the position indicator visible in the upper wall of the housing is colored differently from the rest of the upper wall.

* * * * *

UNITED STATES PATENT AND TRADEMARK OFFICE
CERTIFICATE OF CORRECTION

| | |
|---|---|
| PATENT NO. | : 7,806,692 B2 |
| APPLICATION NO. | : 11/644719 |
| DATED | : October 5, 2010 |
| INVENTOR(S) | : Schaffran et al. |

It is certified that error appears in the above-identified patent and that said Letters Patent is hereby corrected as shown below:

Column 9, line 20 (Claim 15) "therethrouqh" should be changed to --therethrough--

Column 9, line 53 (Claim 16) "Wall" should be changed to --wall--

Signed and Sealed this
Twenty-eighth Day of December, 2010

David J. Kappos
*Director of the United States Patent and Trademark Office*